United States Patent
Stiles

(10) Patent No.: US 9,008,752 B2
(45) Date of Patent: Apr. 14, 2015

(54) METHOD TO DETERMINE DISTRIBUTION OF A MATERIAL BY AN INFUSED MAGNETIC RESONANCE IMAGE CONTRAST AGENT

(71) Applicant: Medtronic, Inc., Minneapolis, MN (US)

(72) Inventor: David Stiles, Danvers, MA (US)

(73) Assignee: Medtronic, Inc., Minneapolis, MN (US)

( * ) Notice: Subject to any disclaimer, the term of this patent is extended or adjusted under 35 U.S.C. 154(b) by 68 days.

(21) Appl. No.: 13/714,563

(22) Filed: Dec. 14, 2012

(65) Prior Publication Data

US 2014/0171781 A1 Jun. 19, 2014

(51) Int. Cl.
| | | |
|---|---|---|
| A61B 5/055 | (2006.01) | |
| A61M 5/14 | (2006.01) | |
| A61M 25/00 | (2006.01) | |
| A61B 5/00 | (2006.01) | |
| G06F 19/00 | (2011.01) | |

(52) U.S. Cl.
CPC ............. *A61B 5/4839* (2013.01); *A61B 5/055* (2013.01); *G06F 19/3437* (2013.01); *G06F 19/3481* (2013.01)

(58) Field of Classification Search
USPC .................. 600/411, 424, 431; 382/128, 131; 606/27, 30, 506
See application file for complete search history.

(56) References Cited

U.S. PATENT DOCUMENTS

| | | | |
|---|---|---|---|
| 5,740,808 A | 4/1998 | Panescu et al. | |
| 5,964,705 A | 10/1999 | Truwit et al. | |
| 5,983,126 A | 11/1999 | Wittkampf | |
| 6,026,316 A | 2/2000 | Kucharczyk et al. | |
| 6,381,485 B1 | 4/2002 | Hunter et al. | |
| 6,464,662 B1 | 10/2002 | Raghavan et al. | |
| 6,482,182 B1 | 11/2002 | Carroll et al. | |
| 6,493,573 B1 | 12/2002 | Martinelli et al. | |
| 6,516,212 B1 | 2/2003 | Bladen et al. | |
| 6,549,803 B1 | 4/2003 | Raghavan et al. | |
| 7,371,225 B2 | 5/2008 | Oldfield et al. | |
| 7,570,791 B2 | 8/2009 | Frank et al. | |
| 7,715,902 B2 | 5/2010 | Hartlep et al. | |
| 7,751,865 B2 | 7/2010 | Jascob et al. | |
| 7,835,778 B2 | 11/2010 | Foley et al. | |
| 8,112,292 B2 | 2/2012 | Simon | |
| 8,295,914 B2 | 10/2012 | Kalafut et al. | |
| 2003/0114752 A1 | 6/2003 | Henderson et al. | |

(Continued)

FOREIGN PATENT DOCUMENTS

| | | |
|---|---|---|
| EP | 1768062 A1 | 3/2007 |
| EP | 07106176 | 4/2007 |

(Continued)

OTHER PUBLICATIONS

BrainLab. 2006 BrainLab AG. Printed in Germany. NS-FL-E-iPlanFLOW Rev. 2.0506 Q:2.000. (2 pages).

(Continued)

*Primary Examiner* — Michael Rozanski
(74) *Attorney, Agent, or Firm* — Harness, Dickey & Pierce, P.L.C.

(57) ABSTRACT

A contrast agent can be infused into a subject and a determination can be made of a VOD and/or a concentration gradient of the contrast agent in the VOD. The contrast agent can be infused in the subject using selected parameters. A correlation to a selected material can be made to determine parameters for infusion the selected material.

20 Claims, 3 Drawing Sheets

(56) References Cited

U.S. PATENT DOCUMENTS

| | | |
|---|---|---|
| 2005/0049486 A1 | 3/2005 | Urquhart et al. |
| 2005/0085714 A1 | 4/2005 | Foley et al. |
| 2005/0085720 A1 | 4/2005 | Jascob et al. |
| 2008/0081982 A1 | 4/2008 | Simon et al. |
| 2009/0270712 A1 | 10/2009 | Raghavan et al. |
| 2010/0240986 A1 | 9/2010 | Stiles |
| 2012/0209110 A1 | 8/2012 | Bankiewicz et al. |
| 2013/0287272 A1 | 10/2013 | Lu et al. |
| 2013/0287275 A1 | 10/2013 | Stiles et al. |
| 2014/0171900 A1 | 6/2014 | Stiles |

FOREIGN PATENT DOCUMENTS

| | | |
|---|---|---|
| EP | 1788499 A1 | 5/2007 |
| EP | 1980201 A2 | 10/2008 |
| WO | WO-2011008982 A1 | 1/2011 |
| WO | WO-2012116747 A1 | 9/2012 |

OTHER PUBLICATIONS

Cabezas, et al. "Areview of atlas-based segmentation for magnetic resonance brain images." Computer Methods and Programs in Bioomedicine. (2011) pp. e158-e177.

Documentation/4.1—SlicerWiki, http://wiki.slicer.org, (2012) p. 1-6.

Linninger, et al., "Annals of Biomedical Engineering." 2007.

Linninger, et al., "Mimic Image Reconstruction for Computer-Assisted Brain Analysis," 2005.

Linninger, et al., "Neurosurg," Focus, 2006, vol. 20.

Morrison PF, et al., "High-flow microinfusion: tissue penetration and phar-acodynamics." Am J Physiol, 1994, vol. 266, R292-R305.

Morrison PF, et al., "High-flow microinfusion: tissue penetration and phar-macodynamics."Am J Physiol, 1994, vol. 266, R292-R305.

Sampson, JH, et al. "Colocalization of gadolinium-diethylene triamine pentaacetic acid with high-molecular-weight molecules after intracerebral convection-enhanced delivery in humans." Neurosurgery, Sep. 2011; 69(3):668-76.

Synchromed II—Infusion system patient manual. (2003) pp. 1-72.

Xiaomin ,Su, et al. "Real-time MR Imaging with Gadoteridol Predicts Distribution of Transgenes After Convection-enhanced Delivery of AAV2 Vectors." The American Society of Gene & Cell Therapy.www.moleculartherapy.org., vol. 18 No. 8, 1490-1495, Aug. 2010.

International Search Report and Written Opinion mailed Jul. 16, 2014 for PCT/US2013/073655 claiming benefit of U.S. Appl. No. 13/714,555 filed Dec. 14, 2012.

International Search Report and Written Opinion for PCT/US2013/073676 mailed Jul. 16, 2014 (claiming benefit of U.S. Appl. No. 13/714,563 filed Dec. 14, 2012).

METHOD TO DETERMINE DISTRIBUTION OF A MATERIAL BY AN INFUSED MAGNETIC RESONANCE IMAGE CONTRAST AGENT

FIELD

The subject disclosure is directed to a method and apparatus for assisting in determining therapy parameters, and particularly to determining a steady state volume of a material infusion based upon a selected set of parameters.

BACKGROUND

This section provides background information related to the present disclosure which is not necessarily prior art.

In providing a selected material for therapy, the selected material can be infused to achieve a therapeutic effect in a therapeutic region in a subject. The subject can include a human patient and the therapeutic region can include the brain, spinal cord and other selected regions. Generally, the material being infused will affect a selected region, such as a region of interest, to achieve a selected outcome.

SUMMARY

This section provides a general summary of the disclosure, and is not a comprehensive disclosure of its full scope or all of its features.

A selected material (also referred to as a therapy material) can be infused into a subject to provide a therapy to the subject. A selected material will generally have a therapeutic effect at a certain concentration in the subject. The volume of the concentration that elicits the desired or selected therapy in the subject is generally termed the volume of efficacy (VOE). The material can be infused into the subject into a volume generally termed the volume of distribution (VOD) which includes the entire three dimensional volume that is contacted by the selected material. The VOE is generally within the VOD and is based on a concentration gradient of the infused material within the VOD. The amount of material infused into the subject is generally termed the volume of infusion (VOI).

The selected material is generally infused into a region of interest (ROI) which can include a region of interest of therapy (ROIT). The ROIT can include portions of a subject, such as spinal cord or brain, including a putamin, a caudate, and other selected regions. Generally a catheter can be provided to or near the selected ROIT to infuse the selected material to the ROIT.

Determining the VOE within the subject can be based upon determining VOD of an infusate into a subject using various techniques. For example, a contrast agent can be infused into a subject and a determination can be made based upon the VOD or a concentration gradient of the infused material in the VOD. The VOD and concentration gradient of the contrast agent can be used to predict a VOD and VOE of the selected material within the subject. The contrast agent can be infused in the subject using selected parameters, as discussed herein, and the subject can then be analyzed to determine a VOD and a concentration gradient to determine a VOE based upon the selected parameters. The contrast agent can include Magnevist® that is a contrast agent viewable in magnetic resonant imaging (MRI) images. In the Magnevist® contrast agent, the contrasty molecule or atom includes gadolinium, which can be present in other branded contrast agent materials.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
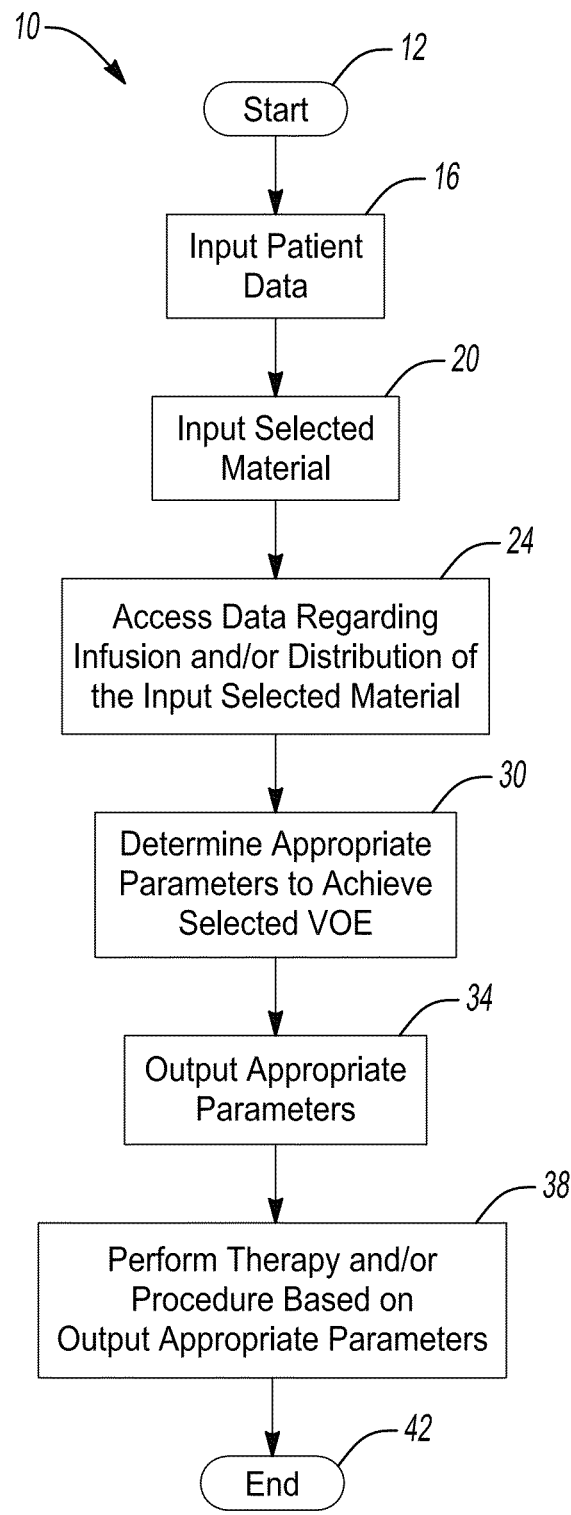
FIG. 1 is a flowchart of a method of determining parameters to generate a selected volume of efficacy in a subject.

According to various embodiments, a method of performing a therapy on a selected subject is illustrated in FIG. 1. A flowchart 10 illustrates a method of performing a therapy on a selected subject using a selected material, the selected material can be a therapy material for performing the therapy. For example, selected materials can include a small inhibiting ribonucleic acid (siRNA), steroids, or other selected materials. The selected materials can include naturally occurring materials, concentrated naturally occurring materials, or synthetic materials. Nevertheless, the selected material can generally be understood to be a drug or pharmaceutical that can be infused into a selected subject, such as a human patient, to provide a therapy to the human patient. The infusion of the selected material can be into selected anatomical regions such as a brain, spinal cord, or other tissue regions. Generally, the method of flowchart 10 allows for the determination of an infusion parameter or set of parameters for achieving a selected therapy in a patient.

According to various embodiments, the method in flowchart 10 can begin in start block 12. The procedure that can proceed to inputting patient data in block 16. Inputting patient data can be inputting selected data regarding the patient, including a disease to be treated, and other patient data. For example, patient data can include image data of the patient, such as image data of a brain. Image data of a brain can include MRI or computed tomography (CT) images. In the image data of the patient, a selected region can be determined, as discussed above including a region of interest for therapy (ROIT). The ROIT can be the area (including a volume in the region) in which a volume of efficacy (VOE) is selected to be achieved. The VOE can be a three dimensional volume within the brain or any selected anatomical region, where the concentration of the selected material is appropriate to achieve a desired or selected result in treating the patient. For example, a VOE of a siRNA can be the volume in which the concentration of the siRNA is enough to achieve inhibition of a selected gene or expression of a gene. Accordingly, input patient data in block 16 can include the determination or selection of an ROIT in an area in which the VOE should be achieved.

Additional inputting of patient data in block 16 can include weighting patient data, inputting patient-specific data including age, alternative or additional diagnoses and other selected information. Weighting the patient data can include weighting image data of the patient to identify the ROIT, regions to not be contacted by the selected material, boundaries or anatomical regions, etc. It is understood, however, that the input patient data in block 16 can include any appropriate data to assist in determining and treating the patient.

Inputting of selected material in block 20 can be inputting the selected material for providing the therapy to the patient. It is understood that inputting the selected material can also be done when inputting the patient data in block 16, but is separated here for clarity of the current discussion. The selected material can be the material that is selected for providing a therapy to the patient and based upon which the VOE can be based. The selected material can be any appropriate material, as noted above, and can include a drug to treat the identified disease of the patient.

Figure 4:
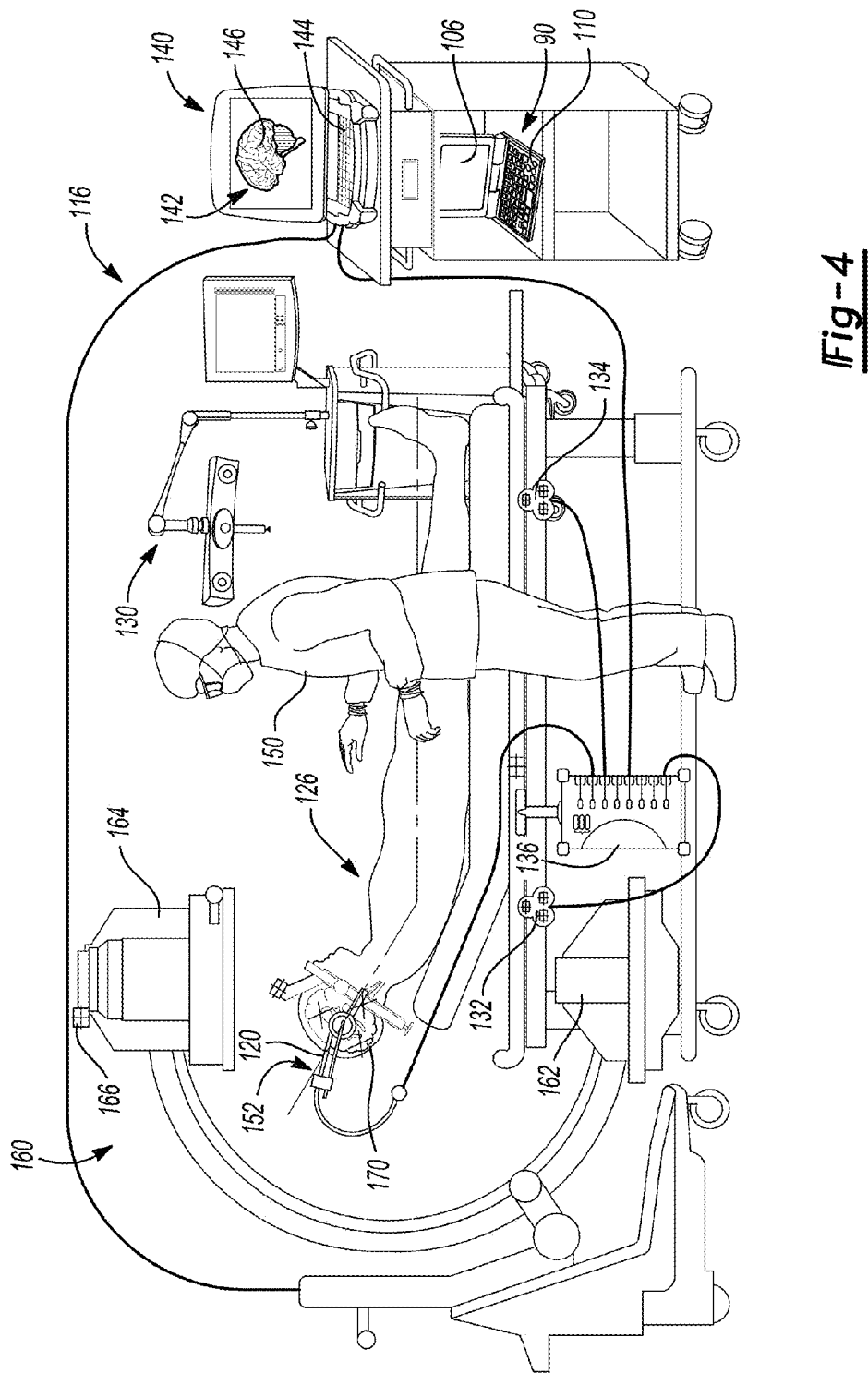
FIG. 4 is a schematic and environmental view of a therapy system.

The selected material input in block 20 can then be used to access data regarding infusion and/or distribution of the input selected material in block 24. That is, accessing data regarding infusion of the selected material can be based upon the selected material input from block 20. Accessing the data in block 24 can be any appropriate accessing, such as accessing a stored database of infusion data regarding a selected material or a plurality of selected materials, inputting infusion parameters of the selected material input in block 20, or other appropriate accessing. For example, as illustrated in FIG. 4, a processor system 90, 140 that can include a processor that is able to access a memory system that has stored in it a database of infusion data. The data access in block 24 can be appropriate data regarding the infusion which can include distribution of the material into a subject, such as into the brain of a human subject, which will be discussed in further detail herein.

The access data regarding infusion of the input selected material in block 24 and the patient data in block 16 can be used to determine parameters to achieve a selected VOE in block 30. Determining appropriate parameters for achieving a selected VOE block 30 can be performed according to various processes. For example, a computer algorithm can be executed as a plurality of instructions by a processor of the processor system 90, 140 to determine a selected VOE and the parameters to achieve the selected VOE. The determination of parameters to achieve the selected VOE can also be based upon other factors, such as the volume of infusion (VOD), the volume of infusion, the position of the VOD and VOE relative to other structures in the patient, and other selected factors. Exemplary systems to determine the parameters for a selected VOE are disclosed in concurrently filed U.S. patent application Ser. No. 13/714,550 incorporated herein by reference. The system, briefly, can analyze the input patient data from block 16, the input selected material from block 20, and the accessed data regarding the input selected material in block 24 to determine at least a VOE and/or a VOD of the selected material in the patient. Various weights and costs factors can then be used to determine a cost of one or more determined VOD and/or VOE in the selected subject. Accordingly, the system can search for or determine, based upon selected parameters and instructions, parameters to achieve the selected VOE in the selected subject that has a lowest cost or cost within a range or threshold.

Once an appropriate set of parameters have been determined in block 30, the parameters can be output in block 34. The parameters can be output in any appropriate manner, such as outputting them as a visual display on a display device (e.g. 106, 142 in FIG. 4), as discussed further herein, for viewing by a user (150 in FIG. 4). Additionally, the output can include a hard copy output, such as a print-out output for assisting in performing and preparing for a therapy. Additionally, it is understood that the parameters can be transferred to a device to provide a therapy to a subject, such as a pump that can pump the selected material to the patient through a catheter (e.g. catheter 120 in FIG. 4).

The parameters can include any appropriate parameters for performing a therapy on a patient. Certain parameters can include infusion parameters that can include a location of an infusion site in the subject. The location of the infusion site can be the specific three dimensional location of an open port of an the infusion catheter 120 within the subject 126. Additionally, the infusion parameters can include the type and/or number of infusion catheters that can be positioned at one or more sites in the subject. The type of infusion catheter can include single port, porous infusion catheters, or multiple port infusion catheters. Additional parameters can include flow rates (including high flow rates and low flow rates) and time at flow rates (including times at high flow rates and times at low flow rates). The infusion parameters can also include the concentration of the selected material for infusion into the patient.

Once the infusion parameters are output in block 34, a therapy can be performed on the patient in block 38. Performing the therapy on the patient can include positioning the infusion catheter in the patient for delivering the selected material to the patient, as illustrated in FIG. 4 and described in further detail below. The catheter can be positioned in the patient using appropriate systems, such as tracking and computer assisted navigation systems for positioning the catheter at the selected location based upon the parameters output in block 34. Appropriate navigation systems can include The StealthStation® surgical navigation systems (including electromagnetic and optical tracking systems), sold by Medtronic, Inc. and those disclosed in concurrently filed U.S. patent application Ser. No. 13/714,550, all of which are incorporated herein by reference. Performing the therapy can then include delivering or infusing the selected material into the patient such as with a pump or other delivery device. It is understood that performing the therapy can include implanting a pump into a patient for a chronic delivery or delivering the material over relatively short period of time for an acute delivery of the therapy.

Once the therapy is completed, either for an acute therapy or a system initially positioned (e.g. including implantation of a pump and positioning of a infusion catheter), the method can end in block 42. The ending of the method can include completing a procedure to position the catheter and pump and delivering an initial dose of therapy, such as in an acute therapy. It is understood that the delivery of a material can include an infusion into the subject and infusion parameters can be used in determining appropriate parameters for achieving a therapy. Convection enhanced diffusion (CED) can be one method of delivering the material for infusion into the subject and can include the infusion, such as with a pump, of a material into the subject.

Figure 2:
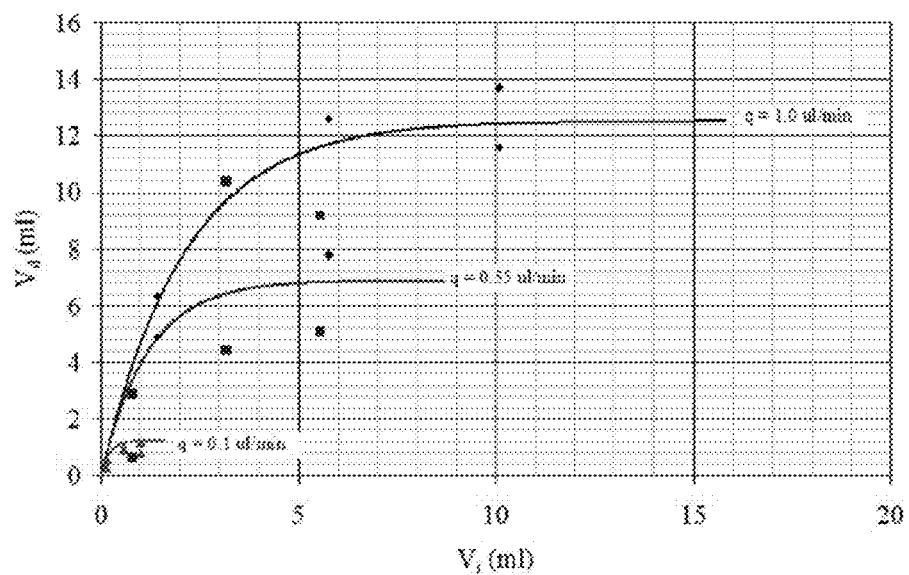
FIG. 2 is a graph of steady state volumes of distribution at differing flow rates.
Figure 3:
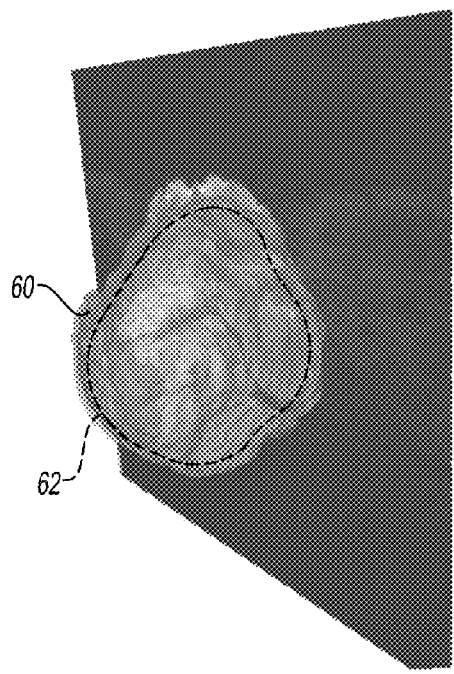
FIG. 3 is an illustration of a correlation of volumes of distribution of a proxy material and a selected material.

With continuing reference to FIG. 1 and additional reference to FIGS. 2 and 3, the accessed data from block 24 can be data that is accessed regarding the selected material. The data that is accessed regarding a selected material can include information relating to the physical flow of the selected material into the patient. The accessed data can also include data regarding interaction of the selected material with the subject, such as pharmacodynamic (PD) and pharmacokinetic (PK) information. Additionally, or as an alternative thereto, information can be determined and stored regarding a flow of a material into a subject. For example, flow of a material can be analyzed to determine a steady-state distribution (SSD) of the material into a subject. The SSD can be based upon selected infusion parameters, including those discussed above, and is a VOD that is reached based on a single set of infusion parameters. At a set period of time, which can be determined based upon analysis or experimentation on the subject, the SSD of the infused material will be achieved and includes a concentration gradient from the point of infusion into the patient to the outer boundary of the SSD. The concentration gradient can be used to determine the volume of distribution and VOE of the selected material into the subject.

The selected material to be infused into the subject, however, can generally be a therapeutic material which can have both beneficial and inhibitive actions on a patient. For example, a pharmaceutical drug that is infused into a patient as the selected material may have beneficial therapies and effects on a patient in a selected concentration and in a selected location, but can have a negative impact on a patient if in a different concentration and/or at a different location. Additionally, certain locations where a drug is administered to are more efficacious than other locations. For example, infusing a drug or selected material into a sulcus may not be very efficacious for the patient. The sulcus or blood pathways can greatly decrease the VOE of the selected material on the patient and causes unselected clearing of the selected material from the patient without allowing time for the selected material to affect the patient.

To assist in determining the VOD, and a concentration gradient within the VOD, a proxy material can be infused, in place of or with, the selected material into a subject or a model of the subject (e.g. a subject model including an animal model). Information determined from the infusion of the proxy material can be used to determine a proxy VOD and a proxy concentration gradient within the subject for which the data is input in block 16. According to various embodiments, a material that is viewable or visible in MRI image data can be infused into the subject model, including rhesus monkeys (Macaca mulatta) as the proxy material. The proxy material can include Magnevist® or other appropriate contrast agents that are available to be infused into a patient. For example, Magnevist® includes a contrast agent gadolinium. A contrast agent can be injected or infused into a patient at selected proxy infusion parameters (such as those infusion parameters discussed above), to generate, during a test or study period, a database or table of proxy VOD and proxy concentration gradients of the proxy material at the proxy infusion parameters. The proxy material information can be obtained by infusing subject models with the contrast agent and imaging of the subject models to identify the proxy VOD and proxy concentration gradient within the VOD of the proxy material.

The proxy VOD and proxy concentration gradient can be correlated to a therapy VOD and therapy concentration gradient of the selected material. In one case, the proxy material can be infused with the proxy infusion parameters into a first subject model and the same parameters can be used to infuse the selected material into a second subject model and a comparison can be made between the two subjects. In an alternative case, the proxy material can also be infused with the selected material simultaneously with the same infusion parameters. A comparison of the proxy material VOD and proxy material concentration gradient with a selected material VOD and selected material concentration gradient can be made. The comparison in the subject model can be used to determine correlation of a VOD and concentration gradient of the proxy material to the selected material. The correlation can then be used to select infusion parameters in the subject of the selected material based on an infusion of the proxy material, as discussed herein.

In one example, the selected material and the proxy material can be injected into the subject model. Imaging the subject model can be performed to view the proxy material VOD and/or proxy material concentration gradient. Various techniques, such as a post-mortem analysis of the subject model, can be made to determine the selected material VOD and concentration gradient of the selected material within the subject model. The comparison of the proxy material VOD and concentration gradient to the selected material VOD and concentration gradient can then be determined and stored as a comparison database or comparison factor, such as in a retrievable database in a memory system. The proxy material can then be injected into the patient and imaging of the patient can occur to determine the proxy material VOD and concentration gradient. Based on the comparison database or comparison factor the predicted selected material VOD and concentration gradient within the patient can be determined. The determination of the predicted selected material VOD and concentration gradient within the patient can be performed by executing a set of instructions with a processor.

For example, as illustrated in FIG. 2, various flow rates (q) can be used to study infusion of materials into the patient or subject model. The flow rates can be studied at a selected concentration and a determination of a steady-state volume of distribution (SSVOD) can be determined as well as the time to achieve the SSVOD. Generally, as illustrated in FIG. 2, the SSVOD occurs when the VOD ($V_d$) remains substantially unchanged over a period of time. The period of time for the steady-state volume can be determined and can be selected to be a time greater than about five days, greater than about seven days, greater than about ten days, or other appropriate timeframe. Accordingly, as illustrated in FIG. 2, the flow rate of the contrast agent (i.e. the proxy material) can be correlated to a VOD and a time to achieve its SSVOD.

As illustrated in FIG. 3, a proxy material steady state VOD (PMVOD) icon 60 can be imaged and viewed, for example on a display device 106, 142 (FIG. 4), to illustrate the SSVOD of the proxy material. A steady state VOD of the selected material can also be illustrated as a selected material steady state VOD (SMVOD) icon 62 on the display device 106, 142. As illustrated in FIG. 3, the PMVOD icon 60 is larger in volume than the SMVOD icon 62, but is correlated by some value. It is also understood that the two VODs may be the same or the SMVOD is larger than the PMVOD. Based on one or more tests in subject models at selected infusion parameters, the correlation between the PMVOD icon 60 and the SMVOD icon 62 can be determined. This correlation can be saved as data in a database on a memory device (such as a memory device in the systems 90, 140 in FIG. 4) for accessing in block 24. It is understood that the PMVOD icon 60 and the SMVOD icon 62 are a graphical illustration of the anatomical or actual volume of distribution of the respective materials at the selected infusion parameters. The discussion herein is to the illustrated icons, but it is understood that the icons can be image data of the actual extent of the respective VODs.

The correlation includes a correlation in difference in volume between the PMVOD icon 60 and the SMVOD icon 62 and the infusion parameters required to achieve the PMVOD icon 60 and the SMVOD icon 62. Thus, the proxy material will have proxy infusion parameters to achieve the PMVOD and the selected material will have therapy infusion parameters to achieve the SMVOD. The correlation can include correlation of the proxy infusion parameters and the therapy infusion parameters. The infusion parameters that can be used to determine the steady-state distribution can include concentration, infusion location (i.e. catheter location), type of catheter, number of catheters, high and low flowrates, and times at high and low flowrates. Nevertheless, it is understood that each of these parameters can be studied to determine the steady-state distribution and concentration gradient in subject models to generate the database of correlations that is accessed in block 24. Further, it is understood the different selected materials may have different correlations with a single proxy material or may require different proxy materials.

Once the correlations of the VODs at the steady-state is determined, the database can then be accessed in block 24 to allow for determination of appropriate parameters to achieve the selected VOE in the selected patient as determined in block 30. The information acquired by analyzing the PMVOD based upon the plurality of proxy infusion parameters is used to determine or correlate to a set of therapy infusion parameters that can be used to achieve the selected VOE, which is a VOD at a selected concentration gradient within the selected subject. The correlation between the PMVOD and SMVOD can be determined to be some proportion of each other. For example, it can be determined that the PMVOD at a set of proxy infusion parameters is 90% of the SMVOD with the same infusion parameters as therapy infusion parameters for the selected material. It is further understood that the concentration of the selected material, the number or position of infusion catheters, and other parameters can be tested and their relation to the SMVOD and PMVOD can also be determined.

Once the correlations of the SMVOD and the PMVOD are determined, including a concentration gradient correlation between them, then only the proxy material need be infused for a therapy test period in the actual subject to determine therapy infusion parameters by accessing the database in block 24. In other words, once a material has been selected the related proxy material is known. The proxy material is generally substantially inert to the subject and can be infused at proxy infusion parameters to determine therapy infusion parameters. Thus, the proxy material can be infused at proxy parameters and the accessed correlation from the database can be used to determine therapy infusion parameters for the selected material based on analyzing the SMVOD.

In one example, the subject can be imaged once the proxy material is infused to a steady state to determine the SMVOD and concentration gradient. The proxy material can include the Magnevist® contrast agent noted above. The subject can then be imaged with a MRI to view the PMVOD, as illustrated in FIG. 3. The database can then be accessed in block 24 to determine therapy parameters for the selected material to achieve a similar or desired VOE and/or SMVOD. The SMVOD icon 62 based on the proxy infusion parameters can be illustrated as well, as illustrated in FIG. 3. The correlation can then be used to determine the therapy parameters and, also based on the determined correlation, the SMVOD and VOE icons can be shown on the display to illustrate them for the user 150.

To plan and perform the therapy, with reference to FIG. 4, a planning system can include a planning processor system 90 that can access a memory system than includes the database from block 24 and execute instructions such as determining the appropriate parameters in block 30. The planning processor system 90 can also include a display device 106 to display the output parameters from block 34. An input device 110 can include a keyboard or other input devices, including a touchscreen or computer input mouse device, to allow for a user to input various parameters and information, including the input patient data from block 16 and the input selected material from block 20.

As further illustrated in FIG. 4, a navigation system 116 can navigate and/or guide the selected catheter 120 into the patient 126 for performing a procedure and applying the therapy in block 38. As discussed above, and incorporated herein by reference, a navigation system is disclosed and described in U.S. patent application Ser. No. 13/714,550 is appropriate and is incorporated herein by reference. Generally, the navigation system 116 can include one or more navigation systems including an optical navigation system having an optical localizer 130 and/or an electromagnetic navigation system including one or more electromagnetic localizers 132 and 134. The electromagnetic localizers 132, 134 can communicate with a localizer array and probe interface 136.

The array controller and probe interface 136, alternatively or in combination with the optical localizer 130, can communicate with a navigation processor system 140. The navigation processor system 140 can include a display device 142 and an input device 144. The display device 142 can display image data 146, such as image data of the patient 126 including that inputted in block 16. The planning processor system 90 and/or the navigation processor system 140 can be operated or used by the user 150 to plan for and/or perform a procedure and therapy on the patient 126, such as performing the therapy in block 38. As discussed above, the instrument 120 can include a catheter that is positioned within the patient 126. The instrument 120 can be passed through an instrument guide 152 into the subject 126. The guide 152 can be navigated with the navigation system 116 that is tracked with either the electromagnetic tracking system or the optical tracking localizer 130.

Additionally, image data can be acquired of the patient 126 such as with a x-ray imaging system 160 that can include an x-ray emission section 162 and an x-ray receiving section 164. The imaging system 160 can be tracked with an imaging system tracking device 166. It is understood that the imaging system 160 can also include other appropriate imaging systems, such as a magnetic resonant imaging (MRI) system, computed tomography (CT), or other appropriate imaging system. Regardless, the instrument 120 can be guided and navigated into a brain 170 of the patient 126 for performing the therapy on the patient 126. It is understood that the patient 126 can be registered to the image data for performing a procedure, as is generally understood in the art and that icons can be displayed on the display device 142 to illustrate the position of the catheter or the instrument 120 relative to the image data 146 displayed on the display device 142.

Additionally, the SMVOE and/or SMVOD can be displayed on the display devices 142 and/or 106 relative to the image data 146 or as separate icons therefrom. The SMVOD, the selected VOE, and/or the PMVOD can be displayed as icons on the display device 106, 142 as illustrated in FIGS. 3 and 4 to illustrate the location of the SMVOD and/or selected VOE relative to the ROIT or other selected regions of the subject. Accordingly, it is understood that a therapy can be planned, such as determining an appropriate set of parameters to achieve a selected VOE, on the planning processor system 90 and a procedure can be performed, such as being able to provide therapy to the subject 126, either directly or using the navigation system 116. Regardless, the data accessed in block 24 can be used to assist in determining the VOD, concentration gradient in the VOD, and/or the VOE of the selected material from block 20 in the selected patient.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of determining a selected set of parameters for a therapy on a subject, comprising:
   selecting a material to provide to the subject for the therapy;
   accessing a database of predetermined parameters related to an infusion of a proxy material in comparison to the selected material;
   executing instructions with a processor to determine infusion parameters to achieve a selected volume of efficacy in the subject of the selected material based on accessing the database of predetermined parameters related to the proxy material; and
   outputting the determined infusion parameters for performing the therapy on the subject.

2. The method of claim 1, wherein the database is based on analyzing image data of at least one of the subject or a subject model after having infused in at least one of the subject or the subject model the proxy material.

3. The method of claim 2, wherein the proxy material includes a magnetic resonance contrast agent.

4. The method of claim 2, further comprising:
   infusing the proxy material into at least one of the subject or the subject model to a steady state distribution with a proxy set of parameters.

5. The method of claim 4, further comprising:
   imaging the subject model with the proxy material at the steady state distribution in the subject;
   determining a proxy volume of distribution of the proxy material at the steady state; and
   determining a concentration gradient of the proxy material within the proxy volume of distribution.

6. The method of claim 5, further comprising:
   correlating the proxy volume of distribution of the proxy material to a selected material volume of distribution of the selected material.

7. The method of claim 6, wherein correlating the proxy volume of distribution of the proxy material to the selected material volume of distribution of the selected material includes infusing the proxy material and the selected material into at least one of the subject or the subject model and comparing the proxy volume of distribution of and a related proxy material concentration gradient to the selected material volume of distribution and a related selected material concentration gradient within the subject model.

8. The method of claim 7, further comprising:
   infusing the proxy material into the subject with a first set of infusion parameters to achieve a steady state proxy material volume of distribution in the subject;
   wherein executing instructions with a processor to determine infusion parameters to achieve a selected volume of efficacy in the subject of the selected material includes evaluating the steady state proxy material volume of distribution in the subject to determine a related selected material volume of distribution at a steady state within the subject.

9. The method of claim 8, wherein executing instructions with a processor to determine infusion parameters to achieve a selected volume of efficacy in the subject of the selected material further includes relating the first set of infusion parameters to a second set of infusion parameters for the selected material to achieve the selected volume of efficacy of the selected material within the subject.

10. The method of claim 9, further comprising:
    displaying the volume of efficacy as an icon superimposed on an image of the subject.

11. A method of determining a selected set of parameters for a therapy on a subject, comprising:
    selecting a material to provide to the subject for the therapy;
    accessing a database of predetermined correlations of parameters relating a proxy material to the selected material;
    analyzing proxy material image data of the subject after having infused in the subject the proxy material to determine a proxy volume of distribution and a proxy concentration gradient within the proxy volume of distribution;
    executing instructions with a processor to determine a therapy infusion parameter for infusion of the selected material to achieve a volume of efficacy in the subject of the selected material based on a proxy infusion parameter; and
    outputting the determined therapy infusion parameter.

12. The method of claim 11, further comprising:
    generating the database by:
       infusing the proxy material and the selected material into a subject model with test infusion parameters;
       comparing a test selected material volume of distribution and concentration gradient with a test proxy material volume of distribution and concentration gradient;
       determining a correlation of the test selected material volume of distribution and concentration gradient and the test proxy material volume of distribution and concentration gradient; and
       saving the correlation in a memory device as the database.

13. The method of claim 12, further comprising:
    infusing substantially only the proxy material into the subject with the proxy infusion parameter prior to analyzing proxy material image data of the subject.

14. The method of claim 13, wherein executing instructions with a processor to determine a therapy infusion parameter for infusion of the selected material includes calculating the therapy infusion parameters based on the determined correlation and the infused substantially only proxy material.

15. The method of claim 11, wherein the proxy infusion parameter and the therapy infusion parameter are identical.

16. The method of claim 15, wherein the proxy infusion parameter and the therapy infusion parameter each include a plurality of parameters.

17. The method of claim 15, wherein the proxy infusion parameter and the therapy infusion parameter each include at least one of a catheter location, a high flow rate, a low flow rate, a time at high flow rate, a time at low flow rate, a proxy material concentration, or a selected material concentration.

18. A system for determining a selected set of parameters for a therapy on a subject, comprising:
- a memory system that stores a database of predetermined correlations of parameters relating a proxy material to a selected material to provide to the subject for the therapy;
- a processor configured to execute instructions to:
  - analyze proxy material image data of the subject after having infused in the subject the proxy material to determine a proxy volume of distribution and a proxy concentration gradient within the proxy volume of distribution,
  - access the memory system to recall a correlation between the proxy material and the selected material, and
  - determine a therapy infusion parameter for infusion of the selected material to achieve a volume of efficacy in the subject of the selected material based on a proxy infusion parameter; and
- a display device configured to display the determined therapy infusion parameter.

19. The system of claim 18, further comprising:
a catheter configured to infuse the proxy material;
a surgical navigation system configured to determine a location of the catheter during the infusion of the proxy material,
wherein the proxy infusion parameter includes the location of the catheter during the infusion of the proxy material.

20. The system of claim 18, further comprising:
a catheter configured to infuse the selected material;
a surgical navigation system configured to determine when the catheter is at a determined infusion location of the catheter for infusion of the selected material;
wherein the therapy infusion parameter includes the determined infusion location.

* * * * *